(12) United States Patent
Ingram et al.

(10) Patent No.: US 7,993,679 B2
(45) Date of Patent: Aug. 9, 2011

(54) FLOWABLE WOUND MATRIX AND ITS PREPARATION AND USE

(75) Inventors: Ronald T. Ingram, Encinitas, CA (US); Jignesh B. Patel, Newtown, PA (US); Timothy J. Pryor, Yardley, PA (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 294 days.

(21) Appl. No.: 12/233,936

(22) Filed: Sep. 19, 2008

(65) Prior Publication Data

US 2009/0092674 A1    Apr. 9, 2009

Related U.S. Application Data

(60) Provisional application No. 60/974,899, filed on Sep. 25, 2007.

(51) Int. Cl.
   *A61K 9/50*    (2006.01)
   *A61K 38/39*   (2006.01)
   *A61K 47/48*   (2006.01)

(52) U.S. Cl. ...................... 424/499; 514/17.2
(58) Field of Classification Search .......... None
   See application file for complete search history.

(56) References Cited

U.S. PATENT DOCUMENTS

| | | | |
|---|---|---|---|
| 4,582,640 A | 4/1986 | Smestad et al. | |
| 4,803,075 A | 2/1989 | Wallace et al. | |
| 4,837,285 A | 6/1989 | Berg et al. | |
| 4,947,840 A | 8/1990 | Yannas et al. | |
| 4,955,893 A * | 9/1990 | Yannas et al. | 606/154 |
| 5,128,136 A | 7/1992 | Bentley et al. | |
| 5,166,187 A | 11/1992 | Collombel et al. | |
| 5,196,185 A | 3/1993 | Silver et al. | |
| 5,397,353 A | 3/1995 | Oliver et al. | |
| 5,476,666 A | 12/1995 | Rhee et al. | |
| 5,629,191 A | 5/1997 | Cahn | |
| 5,658,593 A | 8/1997 | Orly et al. | |
| 6,284,284 B1 | 9/2001 | Naughton | |
| 6,713,083 B1 | 3/2004 | McGregor et al. | |
| 6,911,212 B2 | 6/2005 | Gertzman et al. | |
| 6,929,523 B2 | 8/2005 | Ishii et al. | |
| 6,933,326 B1 | 8/2005 | Griffey et al. | |
| 6,936,271 B1 | 8/2005 | Oliver et al. | |
| 6,969,523 B1 | 11/2005 | Mattern et al. | |
| 7,671,014 B2 | 3/2010 | Beals et al. | |
| 2003/0039676 A1 | 2/2003 | Boyce et al. | |
| 2004/0127987 A1 | 7/2004 | Evans et al. | |
| 2006/0073207 A1 | 4/2006 | Masters et al. | |
| 2007/0161109 A1 | 7/2007 | Archibald et al. | |

OTHER PUBLICATIONS

Moss et al. The effect of chondroitin sulfate on bone healing. Oral Surgery, Oral Medicine, Oral Pathology vol. 20, Issue 6, Dec. 1965, pp. 795-801.*
International Preliminary Report on Patentability relating to corresponding PCT/US08/76975.
International Search Report relating to corresponding PCT/US08/76975.
Written Opinion relating to corresponding PCT/US08/76975.

* cited by examiner

*Primary Examiner* — Marcela M Cordero Garcia
(74) *Attorney, Agent, or Firm* — Banner & Witcoff, Ltd.

(57) ABSTRACT

This invention relates to a flowable collagen/glycosaminoglycan (GAG) material including particles of collagen/GAG matrix that, when hydrated, can be effectively delivered to wounds having varying depths and geometries. The flowable collagen/GAG matrix allows a more intimate contact between the wound matrix and the wound bed, and provides a structural framework that serves as a scaffold for cell ingrowth.

45 Claims, 1 Drawing Sheet

1A

1C

1B

1D

FLOWABLE WOUND MATRIX AND ITS PREPARATION AND USE

RELATED APPLICATION

This application claims priority from U.S. provisional patent application No. 60/974,899, filed Sep. 25, 2007, which is hereby incorporated herein by reference in its entirety for all purposes.

BACKGROUND

1. Field

This invention relates to a flowable matrix material which is composed of particles of collagen matrix, preferably collagen/glycosaminoglycan (GAG) matrix, that, when hydrated, can be effectively delivered to a wound site.

2. Description of Related Art

The majority of chronic and deep tunneling wounds are treated by repeated saline lavage followed by a temporary dressing. The clinical result is generally limited to ineffective tissue repair leading to a continued chronic open wound, infection and/or scarring.

U.S. Pat. No. 4,947,840, which is incorporated herein by reference in its entirety, discloses a biodegradable polymeric material for treating wounds, which acts as a scaffold and induces the wound to synthesize new tissue. The material preferably comprises Type-I collagen and glycosaminoglycan (GAG) in a covalently crosslinked sheet. The material has been shown to reduce contraction and scarring of dermal wounds when used in a sheet form and placed over wounds to promote regeneration. However, when a wound is found to "tunnel" into deep soft tissue, or even bone, and has an irregular geometry, grafting with a sheet form will not be adequate.

Accordingly, it is desired to provide an implant material effective for treating tunneling wounds and wounds having irregular geometries. It is further desired that such a wound dressing material be substantially biodegradable.

BRIEF SUMMARY

This invention relates to a flowable wound matrix material which is comprised of particles of collagen matrix, preferably collagen/glycosaminoglycan (GAG) matrix, that, when hydrated, can be effectively delivered to the wound site. In this configuration, the outcome of wound repair is anticipated to be improved due to the design of the material in the form of particles of collagen/GAG matrix having a porous structure. The flowable wound matrix can be effectively delivered into wounds having varying depths and geometries.

The invention provides a composition comprising collagen particles having a particle size of about 200-2000 micrometers and a pore size of about 10-500 micrometers, and glycosaminoglycan, wherein the composition is flowable. The invention further provides that the particle size ranges from 500 micrometers to 1800 micrometers. The invention further provides that the particle size ranges from 800 micrometers to 1500 micrometers. The invention further provides that the pore size of the particles ranges from 50-350 micrometers. The invention further provides that the pore size of the particles ranges from 70-200 micrometers. The invention further provides that the composition can be sufficiently flowable such that the composition can be placed in a syringe and extruded through a cannula if desired. The invention provides that the composition further comprises a physiologically acceptable fluid. The invention further provides that the glycosaminoglycan is a member selected from the group consisting of chondroitin 6-sulfate, chondroitin 4-sulfate, heparin, heparin sulfate, keratin sulfate, dermatan sulfate, and combinations thereof.

The invention provides that the composition further comprises at least one bioactive molecule effective to enhance wound healing. The invention further provides that the bioactive molecule is a member selected from the group consisting of growth factors, anti-inflammatory agents, wound healing agents, anti-scarring agents, antimicrobial agents, cell adhesion peptides, tissue generation modulating cells, nucleic acids, nucleic acid analogues, proteins, peptides, amino acids, ceramic, and combinations thereof.

The invention further provides that the composition comprises collagen particles having a particle size of about 200-2000 micrometers and the pore size is about 10-500 micrometers, preferably about 50-350 micrometers, and most preferably about 70-200 micrometers. The invention further provides that the composition comprises collagen particles having a particle size of about 500-1800 micrometers and the pore size is about 10-500 micrometers, preferably about 50-350 micrometers, and most preferably about 70-200 micrometers. The invention further provides that the composition comprises collagen particles having a particle size of about 800-1500 micrometers and the pore size is about 10-500 micrometers, preferably about 50-350 micrometers, and most preferably about 70-200 micrometers.

The invention provides a composition comprising collagen particles having a particle size of about 800-1500 micrometers and a pore size of about 70-200 micrometers, and glycosaminoglycan, wherein the composition is flowable.

The invention provides a composition for treating a wound comprising collagen particles and a physiologically acceptable fluid, wherein the collagen particles have a particle size of about 200-2000 micrometers and a pore size of about 10-500 micrometers, which permit cell ingrowth and vascularization. The invention further provides that the collagen particles further comprise glycosaminoglycan. The invention further provides that the collagen particles have a particle size of about 800-1500 micrometers and a pore size of about 70-200 micrometers.

The invention provides a wound dressing kit comprising a first container containing dry particles of collagen and a second container containing a physiologically acceptable fluid, wherein the dry particles of collagen and the physiologically acceptable fluid, when mixed, result in the collagen particles having a particle size of about 200-2000 micrometers and a pore size of about 10-500 micrometers, wherein the collagen particles optionally comprise glycosaminoglycan. The invention further provides that in the kit the composition may be packaged in at least one syringe.

The invention provides a method of altering a condition in an organism by administering the composition to the organism. The invention further provides that the administering comprises contacting a wound with the composition to treat the wound, and the composition optionally further comprises a physiologically acceptable fluid, and may further comprise at least one bioactive molecule. The invention further provides that the administering comprises applying the composition to the organism to provide a matrix in which an additional amount of tissue is generated, and further, wherein the tissue is in a mammal. The invention further provides that the administering comprises contacting a wound of the organism with the composition and the method further comprises subsequently securing the wound with a medically acceptable covering to treat the wound. The invention further provides that the administering comprises applying the composition to a hemorrhaging site to control bleeding.

The invention provides a method of altering a condition in an organism comprising administering a composition to the organism to alter the condition, wherein the composition comprises: (a) collagen particles having a particle size of about 200-2000 micrometers, preferably about 500-1800 micrometers, and most preferably about 800-1500 micrometers and a pore size of about 10-500 micrometers, preferably about 50-350 micrometers, and most preferably about 70-200 micrometers, and (b) glycosaminoglycan, wherein the administering comprises at least one of applying the composition to a wound of the organism, contacting a wound of the organism with the composition to treat the wound, or applying the composition to a hemorrhaging site to control bleeding.

The invention provides a process for preparing a composition comprising collagen particles, comprising providing a sheet of collagen matrix, compressing sheet, and grinding the compressed sheet to produce collagen particles, wherein the collagen particles, when combined with a physiologically acceptable fluid, have a particle size of about 200-2000 micrometers, preferably about 500-1800 micrometers, and most preferably about 800-1500 micrometers and a pore size of about 10-500 micrometers, preferably about 50-350 micrometers, and most preferably about 70-200 micrometers. The invention further provides that the composition comprises a liquid, wherein the proportion of collagen particles to liquid determines the handling characteristics of the composition to enable delivery of the composition to wounds of various sizes and dimensions. The invention further provides that after delivery ability exists for the composition to further expand and fill spaces within a wound bed as the composition absorbs tissue fluids.

The invention provides a method of treating a wound comprising selecting a wound in a patient, providing a container containing collagen particles, providing a container containing a physiologically acceptable fluid, mixing the collagen particles and the fluid to generate a composition comprising collagen particles having a particle size of about 200-2000 micrometers and a pore size of about 10-500 micrometers, and administering the composition to the wound. In a preferred embodiment, the collagen particles further comprise glycosaminoglycan, and have a particle size of about 500-1800 micrometers and a pore size of about 50-350 micrometers.

BRIEF DESCRIPTION OF SEVERAL VIEWS OF THE DRAWINGS

The invention will be described in conjunction with the following drawings wherein:

FIGS. 1A and 1B (left panels) show the deep muscle wound two weeks after administration of the flowable wound matrix (Top 10×; Bottom 200×). FIGS. 1C and 1D (right panels) show the deep muscle wound eight weeks after administration of the flowable wound matrix (Top 10×; Bottom 400×).

DETAILED DESCRIPTION OF CERTAIN PREFERRED EMBODIMENTS

Figure 1:
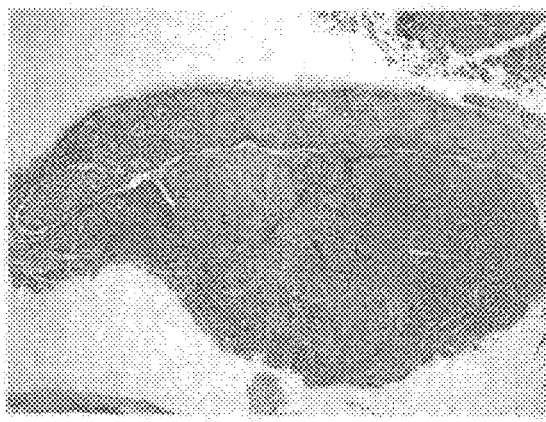
FIG. 1 is a photomicrograph of Guinea Pig deep muscle wound at 2 and 8 weeks following administration of an embodiment of the flowable wound matrix of the invention.
Figure 1:
Figure 1:
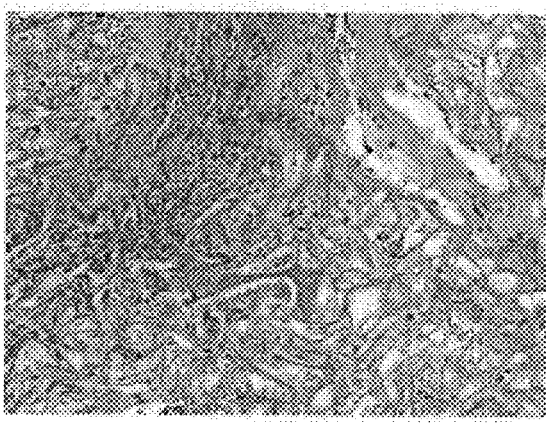
Figure 1:
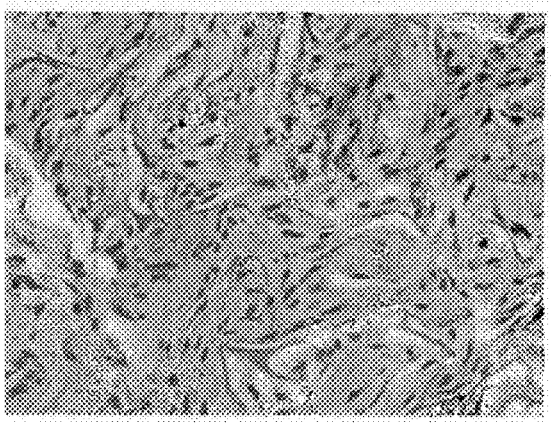

For treatment of wounds having irregular geometries such as tunneling wounds, a more intimate contact between the wound matrix and the wound bed will facilitate more complete and rapid tissue regeneration. This can be accomplished with the gel-like wound matrix of the invention which can be administered through, for example, a syringe with a flexible tip. The composition of the invention comprises particles of collagen matrix. The composition may further comprise glycosaminoglycan (GAG). The method of administration of the instant invention allows for more complete coverage in deep creviced wounds.

In an exemplary embodiment, a collagen/GAG sheet is used as a starting material in manufacturing, and further processed in a mill or grinder, in either a wet or dry form to yield particulates of the original sheet. The particulates are of appropriate size such that, when hydrated, they can be extruded from a syringe-type delivery system into a wound bed, yet of sufficient size to provide a structural framework that serves as a scaffold for cell ingrowth and vascularization. The particles, in a hydrated form, have particle sizes of, for example, 200-2000 micrometers, preferably 500-1800 micrometers, and most preferably 800-1500 micrometers. The particles contain sufficient structural matrix containing pores ranging in size from 10-500 micrometers, preferably 50-350 micrometers, and most preferably 70-200 micrometers to provide a scaffold for cell ingrowth and vascularization.

The flowable collagen/GAG wound matrix can be processed from sheets of collagen/GAG matrix into particles that include preferably both large and small sizes. By utilizing different proportions of large and small collagen particles, a range of handling characteristics can be achieved to enable delivery to wounds of differing sizes and dimensions. When hydrated, the large particles absorb and expand to about 200-400% of their dry size.

Collagen is the major protein component of bone, cartilage, skin, and connective tissue in animals. Collagen occurs in several "types," having differing physical properties. The most abundant types are Types I, II and III. The flowable wound matrix is a particulate flowable collagen/GAG material which is composed of, for example, particles of type-I collagen/glycosaminoglycan (GAG) matrix that, when hydrated, can be effectively delivered to a wound site.

In an exemplary embodiment, the particles of the flowable wound matrix will be mixed with saline solution at the time of application to form a gel/putty like consistency. This flowable wound matrix can be used, for example, for the treatment of diabetic foot ulcers and other wounds where a flowable matrix is appropriate. The flowable wound matrix can augment wound closure in deep, hard-to-access wounds and can have a convenient delivery mechanism (for example, syringe with a flexible angiocath tip). This allows for more complete coverage and intimate contact with the wound bed in a minimally invasive manner.

The term "flowable" as used herein applies to compositions whose consistencies range from those which can be described as shape-sustaining but readily deformable, e.g., those which behave like putty, to those which are gel like, to those which are runny. In an exemplary embodiment of the invention, the flowable composition is capable of passing through a syringe and cannula.

The invention provides a flowable wound matrix material which comprises, for example, particles of type-I collagen/glycosaminoglycan (GAG) matrix that, when hydrated, can be effectively delivered to a wound site. Due to its flowable nature the product will achieve a more intimate contact between the matrix and the surrounding tissue walls. This intimate contact will facilitate more complete and rapid vascularization and cell ingrowth. Due to its flowable nature the flowable wound matrix can reduce the voids and open spaces and thereby reduce fluid build up that can be associated with a reduction in tissue regeneration and increase susceptibility to infection. The invention provides the use of particles comprising, for example, highly purified Type-I collagen and the proteoglycan, chondroitin sulfate, wherein a high degree of biocompatibility with the host tissue will be achieved and the ability of cells and vascularization to bind and grow into the material will be improved.

The invention provides a flowable collagen-based material in which the collagen, either alone or in combination with a glycosaminoglycan, a glycoprotein, a structural protein or a growth factor is crosslinked. Suitable glycoproteins include, but are not limited to, fibronectin, laminin and chondronectin. An example of a suitable structural protein is elastin. Growth factors include but are not limited to, epidermal growth factor (EGF), platelet derived growth factor (PDGF), vascular endothelial growth factor (VEGF), fibroblast growth factor (FGF), nerve growth factor (NGF), bone morphogenetic protein (BMP), and the like.

The invention further provides the use of chemical crosslinking of the collagen that is controlled during manufacturing, so that a degradation rate can be attained that is conducive to the rate of tissue regeneration. Due to the degree of crosslinking during manufacturing, the product is rendered less susceptible to the increased degradation imparted by the mode of sterilization based on exposure to high energy radiation (e-beam or gamma).

The invention provides the use of a range of particle sizes of, for example, about 200-2000 micrometers, preferably about 500-1800 micrometers, and most preferably about 800-1500 micrometers. The particles are rendered flowable as a means to improve application and delivery through, for example, a syringe and cannula. The material has improved handling characteristics for delivery. The invention further provides the use of a structural matrix having a pore size range of, for example, about 10-500 micrometers, preferably about 50-350 micrometers, and most preferably about 70-200 micrometers, cells and vascularization can gain full access to the internal regions of the structural matrix thereby improving the ability of the material to regenerate tissue.

The invention further provides the use of a physiologically acceptable fluid, for example, an aqueous based diluent. Physiologically acceptable fluid refers to any fluid or additive suitable for contacting biological material. Exemplary physiologically acceptable fluids include but are not limited to preservative solutions, buffer solutions, saline solutions, water and lactated Ringer's solution. It is intended that the present invention is not to be limited by the type of physiologically acceptable fluid used. The invention further provides that through the use of an appropriate range of ratios between the solid and liquid components, the desired material handling and delivery properties are achieved. By utilizing different proportions of solid to liquid, a range of handling and delivery characteristics that enable delivery to wounds of differing sizes and dimensions can be achieved.

The invention further provides the option to use the flowable wound matrix material in conjunction with a range of other fluid-based constituents including, for example, blood-derived materials (such as fibrin, platelet rich plasma, bone marrow aspirate), growth factors, antimicrobials, thrombogenics, and the like depending on the type and condition of the wound.

The flowable wound matrix of the instant invention maintains a three dimensional structure comprising a structural matrix with a range of particle sizes from, for example, about 200-2000 micrometers, preferably about 500-1800 micrometers, and most preferably about 800-1500 micrometers, having a pore size range of, for example, about 10-500 micrometers, preferably about 50-350 micrometers, and most preferably about 70-200 micrometers, which permits cell ingrowth and tissue regeneration.

The invention further provides a process to generate the particles of collagen/GAG matrix under wet and dry conditions. Due to the use of a process that, for example, effectively "collapses" the collagen sheet during manufacturing: (a) the porous matrix is protected from high shear forces during the milling procedure that would otherwise compromise the structure; (b) upon hydration the particles rapidly expand back to the preset dimensions to form the structural matrix of the product; and/or (c) upon hydration the particles rapidly expand back to the preset dimensions based on the liquid to solid ratio with the ability to further expand as a means to continue to provide good contact with the walls of the defect by absorbing wound fluid. By production and packaging in a dry form, the product has improved stability. The process also allows porous structures to be protected during the manufacturing process. The process yields a material that after delivery, retains an ability to further expand and fill spaces within the wound bed as is absorbs tissue fluids.

An exemplary method of producing the flowable wound matrix of the instant invention comprises a lyophilization step. A dispersion of, for example, bovine tendon collagen is prepared and, for example, glycosaminoglycan (GAG) can optionally be added to the dispersion. The dispersion is then frozen and lyophilized to dryness. As it freezes, it forms crystals and the crystals drive the collagen away from the crystals, which creates pores in the collagen matrix structure upon removal of the frozen water. For generation of the particles, collagen sheets are first saturated with de-ionized water. Each collagen/GAG sheet is then compressed to remove de-ionized water. The collagen, with optional GAG, sheet is then soaked in isopropyl alcohol (IPA), which is subsequently removed by light compression of the collagen sheets. Each sheet is flattened and exposed to air flow to accelerate removal of remaining IPA. The sheets are briefly soaked in liquid nitrogen. The sheets are then ground to particles of 20-2000 micrometers, preferably 500-1800 micrometers, and most preferably 800-1500 micrometers in size, while maintaining a pore size of, for example, 10-500 micrometers, preferably 50-350 micrometers, and most preferably 70-200 micrometers.

In a further exemplary embodiment, the flowable wound matrix of the instant invention is cross-linked. Collagen can be crosslinked using methods generally known in the art, such as by heat, radiation, or using conventional chemical crosslinking agents such as, for example, aldehydes, carbodiimides, epoxides, or imidazoles. Covalent crosslinking can be achieved by many specific techniques with the general categories being chemical, radiation and dehydrothermal methods. An advantage to most crosslinking methods contemplated, including glutaraldehyde crosslinking and dehydrothermal crosslinking, is that they also serve to remove bacterial growths from the materials. Thus, the composites become sterilized while simultaneously being crosslinked. One suitable method for covalently crosslinking the collagen-GAG composites is known as aldehyde crosslinking. In this process, the materials are contacted with aqueous solutions of aldehyde, which serve to crosslink the materials. Suitable materials include formaldehyde, glutaraldehyde and glyoxal. Another crosslinking method is referred to herein as a dehydrothermal process. In dehydrothermal crosslinking, no external crosslinking agents need to be added to the composite. Rather, the composite is dehydrated to a moisture content of less than about 1% under vacuum. The actual amount of water which must be removed will vary with many factors, but, in general, sufficient water to achieve the desired crosslinking density must be removed. Thus, a collagen/GAG product can be subjected to elevated temperatures under vacuum conditions until the moisture content is reduced to extremely low levels and the desired crosslinking density is achieved.

In addition to the flowable collagen particles, the composition of the invention includes, for example, a physiologically acceptable fluid and glycosaminoglycan (GAG) molecules, such as hyaluronic acid or chondroitin sulfate. In an exemplary embodiment the present invention comprises collagen and GAG. Various forms of GAG which may be suitable for use in this material include, but are not limited to, hylauronic acid, chondroitin 6-sulfate, chondroitin 4-sulfate, heparin, heparin sulfate, keratin sulfate and dermatan sulfate. Other types of molecules that can be used in combination with collagen during the manufacturing process include, but are not limited to, chitin, chitosan, fibronectin, laminin, and the like, or combinations thereof.

The flowable wound matrix of the invention can further comprise bioactive molecules effective to achieve a desired result. Suitable bioactive molecules include, but are not limited to, growth factors, anti-inflammatory agents, wound healing agents, anti-scarring agents, antimicrobial agents (for example, silver), cell-adhesion peptides including Arg-Gly-Asp (RGD) containing peptides, nucleic acids, nucleic acid analogues, proteins, peptides, amino acids, and the like, or combinations thereof.

Pharmacologically active agents such as, for example, VEGF (vascular endothelial cell growth factor), FGF (the fibroblast growth factor family of proteins), TGFβ (transforming growth factor B), hepatocyte growth factor (HGF), platelet factor 4 (PF4), PDGF (platelet derived growth factor), EGF (epidermal growth factor), NGF (nerve growth factor), BMP (bone morphogenetic protein family), coagulation factors such as one of the vitamin K-dependent coagulant factors, such as Factor II/IIa, Factor VII/VIIa, Factor IX/IXa or Factor X/Xa. Factor V/Va, VIII/VIIIa, Factor XI/XIa, Factor XII/XIIa, Factor XIII/XIIIa, and mixtures thereof may also be used. Antibiotics, antifungal agents, hormones, enzymes, enzyme inhibitors, and mixtures thereof can also be incorporated in the compositions of the instant invention and subsequently delivered to the wound site.

Various particulate materials may also be incorporated into biomaterial compositions for use in the invention. Examples of suitable particulate materials include, but are not limited to, ceramic particles (preferably hydroxyapatite and/or tricalcium phosphate, which are particularly useful, for example, for the repair of bone); particulate crosslinked or non-crosslinked fibrillar collagen; poly(lactic) acid (PLA), poly(glycolic) acid (PGA), and copolymers thereof (PLGA); chitosan, calcium carbonate; calcium sulfate; calcium phosphate, hyroxyapatitie, bioactive glass, gelatin beads; polytetrafluoroethylene beads; silicone rubber beads; beads of various hydrogel polymers (such as polyacrylonitrile-polyacrylamide hydrogels); silicon carbide beads; and glass beads.

In addition, the delivered composition can include blood-derived fluids, cells and cell concentrates of autologous, allogeneic and/or xenogeneic origin. Blood-derived fluids include, but are not limited to, for example, platelet-rich plasma, fibrin, buffy coat. Cells include, but are not limited to, for example, fresh, cultured or transfected origin and can be derived from bone marrow cells, cell isolates from organs or tissues, mesenchymal stem cells and may be diluted or concentrated.

Administration of therapeutically effective amounts of the flowable wound matrix composition is by any of the routes normally used for introducing materials into ultimate contact with the tissue to be treated. The composition is administered in any suitable manner. Suitable methods of administering such compositions are available and well known to those of skill in the art, and, although more than one route can be used to administer a particular composition, a particular route can often provide a more immediate and more effective reaction than another route. The composition can be administered, for example, by topical, subdermal, intramuscular, subcutaneous or interfascial means to reach the desired wound site.

In an exemplary embodiment, the invention provides a method of delivery of the material to a wound site via a syringe-based system that allows addition of other desirable bioactive molecules including but not limited to, blood products, bone marrow aspirate, platelet rich plasma, growth factors, antibiotics, antimicrobials, cytokines, thrombogenics, and the like prior to extrusion into the wound site.

The invention provides a delivery system in kit form which includes, in an amount sufficient for at least one administration, the flowable wound matrix composition of the present invention in packaged form.

As used herein, the term "package" refers to a solid matrix or material such as glass, plastic, paper, foil and the like capable of holding within fixed limits the flowable wound matrix composition of the present invention. The package may be, for example, at least one syringe. The package may be more than one syringe. The at least one syringe may optionally comprise a flexible tip. The flowable wound matrix can be presented in unit-dose or multi-dose sealed containers, such as ampules and vials, or syringe dosage forms for administration by cannula or flexible tip.

The invention provides a composition in kit form. The kit may comprise a single container means that contains both collagen particles and a physiologically acceptable fluid. The container means may itself be a syringe, pipette, or other such like apparatus, from which the collagen particles material may be applied to, for example, a wound area or other target site. However, the single container means may contain dry collagen particles, which may or may not require pre-wetting before use. The collagen particles may comprise GAG.

Alternatively, the kits of the invention may comprise distinct container means for each component. In such cases, one container could contain, for example, the collagen particles, and the other container could include, for example, the physiologically acceptable fluid.

The kits may also comprise one or more container means for containing a sterile, pharmaceutically acceptable fluid oroptional components. Such a solution may be required to formulate the matrix component, both components separately, or a pre-mixed combination of the components, into a more gelatinous form for application to the body. It should be noted, however, that components of a kit could be supplied in a dry form, which would allow for "wetting" upon contact with body fluids. Thus, the presence of any type of physiologically acceptable fluid is not a requirement for the kits of the invention.

The container means will generally be a container such as a vial, test tube, flask, bottle, syringe, or other container means, into which the components of the kit may be placed. The components may also be aliquoted into smaller containers, should this be desired. The kits of the present invention may also include a means for containing the individual containers in close confinement for commercial sale, such as plastic containers into which the desired vials or syringes are retained.

The kits of the invention may also comprise, or be packaged with, an instrument for assisting with the placement of the collagen particle composition onto or within the body of an animal, for example, a mammal. Such an instrument may be a syringe, pipette, forceps, or any such medically approved delivery vehicle.

The compositions of the invention are useful for treating a wide variety of conditions in a wide variety of organisms, including mammals, and in particular humans. The flowable wound matrix is useful for, for example, the management of wounds including but not limited to: partial and full-thickness wound, pressure ulcers, venous ulcers, diabetic ulcers, chronic vascular ulcers, tunneled/undermined wounds, surgical wounds (donor sites/grafts, Post-Moh's surgery, post-laser surgery, podiatric wound dehiscence), trauma wounds (abrasions, lacerations, second degree burns, skin tears), and draining wounds. An example of the utility of the flowable wound matrix is for treating a range of wound types including shallow and deep wounds of varying dimensions and geometries and at differing conditions (acute/chronic).

In addition, the compositions can be employed to, for example, augment tissue, generate tissue in situ, reduce scar formation, deliver gene therapy agents, treat topical wounds, treat surgical wounds, treat deep tunneling wounds, treat trauma wounds, control bleeding. In addition, the compositions can be, for example, applied into or adjacent to a target tissue of an organism to enhance vascularization of target tissue, applied into or adjacent to a fractured or diseased bone of the organism to enhance repair of the fractured or diseased bone, placed into a herniated spinal disk of an organism through an entry site to surgically correct the herniated spinal disk, or applied into or adjacent to a prosthetic device, to enhance integration of the prosthetic device into tissue of an organism.

The invention will be illustrated in more detail with reference to the following Examples, but it should be understood that the present invention is not deemed to be limited thereto.

EXAMPLES

Example 1

Preparation of the Flowable wound matrix. A dispersion of bovine tendon collagen is prepared at a concentration of 0.1% to 2.0% wt:vol, preferably about 0.75%. Glycosaminoglycan (GAG) can optionally be added to the dispersion at a concentration of 0.1% to 20% wt:wt with reference to the amount of collagen. The dispersion is then placed into a suitable casting mold, typically a stainless steel tray, to a depth of 1 mm to 10 mm, preferably about 2 mm. The dispersion is then frozen and lyophilized to dryness.

The collagen matrix obtained from this process is then dehydro-thermally treated by placing the matrix into a vacuum oven and heating to approximately 105° C. under vacuum for 18 to 24 hours. The DHT crosslinked collagen matrix is then chemically crosslinked by immersing the collagen matrix in 0.5% Gluteraldehyde for 2 to 24 hours. The chemically crosslinked collagen matrix is then thoroughly rinsed with PBS and deionized water.

Each collagen/GAG sheet is compressed to remove Deionized Water (WFI)/Phosphate Buffer Solution (PBS). The collagen/GAG sheet is soaked in 99% Isopropyl Alcohol (IPA) for 60 minutes. The majority of IPA is removed by compression of the collagen sheets. Repeat 99% IPA soak and removal by compression. Each sheet is flattened and exposed to air flow to accelerate removal of remaining IPA and collapse the matrix. The sheets are soaked in liquid nitrogen. The sheets are then ground (e.g. Wiley Mill) to particles of about 20-2000 micrometers, about 500-1800 micrometers, or about 800-1500 micrometers in size. The particles are dispensed into a syringe using a metered dispenser, packaged and sterilized (for example by E-beam or Gamma).

Example 2

Referring to FIG. 1, flowable collagen/GAG matrix are generated and delivered in a flowable form from a syringe fitted with a large gauge needle. The material was tested in a guinea pig deep muscle wound and evaluated after 2, 4 and 8 weeks with favorable cell and vascular ingrowth and tissue response. Using an approved protocol and following strict animal use guidelines, the flowable collagen material was injected into approximately 6 mm×6 mm defects in the dorsal muscle of guinea pigs. After 2, 4, and 8 weeks, the animals were euthanized and a histological analysis was performed on the treated wound sites. FIG. 1 shows representative photomicrographs of cross-sections of a formalin fixed, H&E stained tissue across the wound site for the 2 and 8 week time points. Good contact between the wound margins and the implanted material can be seen. A robust cellular in-growth is clearly visible with significant amounts of new collagen and extracellular matrix evident surrounding the cells over time. Small capillary ingrowth is also visible at the margins of the injection site. The histological evidence suggests a normal pattern of wound healing and the formation of native-like tissue. No evidence of adverse tissue reaction or excessive fibrosis was noted.

Example 3

Determination of Particle Size. The particle size of the flowable wound matrix material was measured by a laser diffraction type particle size analyzer and found to be in the range of about 500-1800 micrometers.

Example 4

The flowable wound dressing kit according to the invention is provided sterile, in single use kits containing one syringe with dry granular collagen/GAG, one syringe with phosphate buffer saline, one connector and one angiocath tip. It can be stored at room temperature.

Example 5

To use the flowable wound dressing as described in Example 4, the following steps are to be followed: (1) Prepare wound bed using standard methods to ensure wound is free of debris and necrotic tissue. (2) Remove tip cap from the dry collagen/GAG syringe and attach the connector to the collagen/GAG syringe. (3) Remove tip cap from saline syringe and attach to open end of the connector. (5) Hold both syringes and dispense saline into the collagen/GAG syringe with normal force. (6) Depress plungers back and forth between the syringes for at least 15 times. (7) Consider the mixture/putty ready when product appearance is consistent and homogeneous. (8) Ensure all material is moved into one syringe. (9) Remove the connector. (10) Attach the angiocath tip to the syringe. (11) Dispense the material at the desired location filling defects or voids to minimize dead space. (12) After application, a secondary dressing can be applied to maintain dressing adherence and protect the wound area. The secondary dressing is selected depending on wound location, size, depth and user preference.

While the invention has been described in detail and with reference to specific examples thereof, it will be apparent to one skilled in the art that various changes and modifications can be made therein without departing from the spirit and scope thereof.

What is claimed is:

1. A composition comprising:
   hydrated, collagen particles expanded 200 to 400% of their dry size having in hydrated form a particle size of about 200-2000 micrometers and a pore size of about 10-500 micrometers; and
   glycosaminoglycan,
   wherein the composition includes a physiologically acceptable fluid and is flowable.

2. The composition of claim 1, wherein the particle size ranges from about 500-1800 micrometers.

3. The composition of claim 1, wherein the particle size ranges from about 800-1500 micrometers.

4. The composition of claim 1, wherein the pore size of the particles ranges from about 50-350 micrometers.

5. The composition of claim 1, wherein the pore size of the particles ranges from about 70-200 micrometers.

6. The composition of claim 1, wherein the composition is sufficiently flowable such that the composition can be placed in a syringe and extruded through a cannula.

7. The composition of claim 1, wherein the glycosaminoglycan is selected from the group consisting of chondroitin 6-sulfate, chondroitin 4-sulfate, heparin, heparin sulfate, keratin sulfate, dermatan sulfate, and combinations thereof.

8. The composition of claim 1, further comprising at least one bioactive molecule effective to enhance wound healing.

9. The composition of claim 8, wherein the bioactive molecule is a member selected from the group consisting of growth factors, anti-inflammatory agents, wound healing agents, anti-scarring agents, antimicrobial agents, cell adhesion peptides, tissue generation modulating cells, nucleic acids, nucleic acid analogues, proteins, peptides, amino acids, ceramic, and combinations thereof.

10. The composition of claim 2, wherein the pore size is about 50-350 micrometers.

11. The composition of claim 2, wherein the pore size is about 70-200 micrometers.

12. The composition of claim 3, wherein the pore size is about 50-350 micrometers.

13. The composition of claim 3, wherein the pore size is about 70-200 micrometers.

14. The composition of claim 1, further comprising a liquid, wherein the proportion of collagen particles to liquid determines the handling characteristics of the composition to enable delivery of the composition to wounds of various sizes and dimensions.

15. The composition of claim 1, wherein after delivery sufficient ability exists for the composition to further expand and fill spaces within a wound bed as the composition absorbs tissue fluids.

16. A composition comprising hydrated, collagen particles expanded 200 to 400% of their dry size having in hydrated form a particle size of 200-2000 micrometers and a pore size of 10-500 micrometers;
   wherein the composition includes a physiologically acceptable fluid and is flowable.

17. The composition of claim 16, wherein the collagen particles have a particle size of 500-1800 micrometers and a pore size of 50-350 micrometers.

18. The composition of claim 16, wherein the collagen particles have a particle size of 800-1500 micrometers and a pore size of 70-200 micrometers.

19. The composition of claim 16, further including glycosaminoglycan.

20. A composition for treating a wound comprising hydrated, collagen particles expanded 200 to 400% of their dry size and a physiologically acceptable fluid, wherein the collagen particles in hydrated form have a particle size of about 200-2000 micrometers and a pore size of about 10-500 micrometers, which permit cell ingrowth and vascularization.

21. The composition claim 20, further including glycosaminoglycan.

22. The composition of claim 21, wherein the collagen particles have a particle size of about 500-1800 micrometers and a pore size of about 50-350 micrometers.

23. The composition of claim 21, wherein the collagen particles have a particle size of about 800-1500 micrometers and a pore size of about 70-200 micrometers.

24. A wound dressing kit comprising a first container containing dry particles of collagen and a second container containing a physiologically acceptable fluid, wherein the dry particles of collagen and the physiologically acceptable fluid, when mixed, result in hydrated, collagen particles expanded 200 to 400% of their dry size having in hydrated form a particle size of about 200-2000 micrometers and a pore size of about 10-500 micrometers, wherein the wherein the first container optionally includes glycosaminoglycan.

25. The kit of claim 24, wherein at least one of the first and second containers is a syringe.

26. A method of treating an organism having a wound, said method comprising administering the composition of claim 1 to the organism to treat the wound.

27. The method of claim 26, wherein the composition further comprises a physiologically acceptable fluid.

28. The method of claim 26, wherein the composition further comprises at least one bioactive molecule.

29. The method of claim 26, wherein the administering comprises applying the composition to the organism to provide a matrix in which an additional amount of tissue is generated.

30. The method of claim 29, wherein the tissue is in a mammal.

31. The method of claim 26, wherein the administering comprises contacting a wound of the organism with the composition and the method further comprises subsequently securing the wound with a medically acceptable covering to treat the wound.

32. The method of claim 26, wherein the administering comprises applying the composition to a hemorrhaging site to control bleeding.

33. The method of claim 26, wherein the condition is selected from the group consisting of: partial and full-thickness wound, pressure ulcers, venous ulcers, diabetic ulcers, chronic vascular ulcers, tunneled/undermined wounds, surgical wounds, trauma wounds, and draining wounds.

34. A method of controlling bleeding in an organism, said method comprising administering a composition to the organism to alter the condition, wherein the composition comprises: (a) hydrated collagen particles expanded 200 to 400% of their dry size having in hydrated form a particle size of about 200-2000 micrometers and a pore size of about 10-500 micrometers, and (b) glycosaminoglycan, wherein the administering comprises at least one of:
   applying the composition to a wound of the organism;
   contacting a wound of the organism with the composition to treat the wound;
   applying the composition to a hemorrhaging site to control bleeding.

35. The method of claim 34, wherein the collagen particles have a particle size of 500-1800 micrometers and a pore size of 50-350 micrometers.

36. The method of claim 34, wherein the collagen particles have a particle size of 800-1500 micrometers and a pore size of 70-200 micrometers.

37. A process for preparing a composition comprising collagen particles, comprising:
providing a sheet of collagen matrix;
compressing said sheet; and
grinding the compressed sheet to produce collagen particles,
wherein said collagen particles, when combined with a physiologically acceptable fluid, expand to 200 to 400% of their dry size, have in hydrated form a particle size of about 200-2000 micrometers, and a pore size of about 10-500 micrometers.

38. The process of claim 37, wherein the collagen particles have a particle size of 500-1800 micrometers and a pore size of 50-350 micrometers.

39. The process of claim 37, wherein the collagen particles have a particle size of 800-1500 micrometers and a pore size of 70-200 micrometers.

40. A method of treating a wound comprising:
selecting a wound in a patient;
providing a container containing collagen particles;
providing a container containing a physiologically acceptable fluid;
mixing the collagen particles and the fluid to generate a composition comprising hydrated collagen particles expanded to 200 to 400% of their dry size having in hydrated form a particle size of about 200-2000 micrometers and a pore size of about 10-500 micrometers; and
administering the composition to the wound.

41. The method of claim 40, wherein the collagen particles further comprise glycosaminoglycan, and have a particle size of about 500-1800 micrometers and a pore size of about 50-350 micrometers.

42. The composition of claim 40, wherein the collagen particles have a particle size of 800-1500 micrometers and a pore size of 70-200 micrometers.

43. A composition comprising collagen particles prepared by the process of providing a sheet of collagen matrix;
compressing said sheet; and
grinding the compressed sheet to produce dry collagen particles,
wherein said dry collagen particles, when combined with a physiologically acceptable fluid produce hydrated, collagen particles expanded to about 200 to 400% of their dry size having in hydrated form a particle size of about 200-2000 micrometers, and a pore size of about 10-500 micrometers.

44. The composition of claim 43, wherein the collagen particles have a particle size of 500-1800 micrometers and a pore size of 50-350 micrometers.

45. The composition of claim 43, wherein the collagen particles have a particle size of 800-1500 micrometers and a pore size of 70-200 micrometers.

* * * * *